(12) United States Patent
Koyama et al.

(10) Patent No.: US 11,931,133 B2
(45) Date of Patent: *Mar. 19, 2024

(54) MEASURING DEVICE, METHOD OF MEASURING BLOOD PRESSURE, AND PROGRAM

(71) Applicant: NIHON KOHDEN CORPORATION, Tokyo (JP)

(72) Inventors: Yukio Koyama, Tokyo (JP); Yoshiharu Harada, Tokyo (JP); Masami Tanishima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 214 days.

This patent is subject to a terminal disclaimer.

(21) Appl. No.: 14/927,909

(22) Filed: Oct. 30, 2015

(65) Prior Publication Data

US 2016/0128584 A1 May 12, 2016

(30) Foreign Application Priority Data

Nov. 10, 2014 (JP) .................................. 2014-227656

(51) Int. Cl.
*A61B 5/0215* (2006.01)
*A61B 5/00* (2006.01)

(52) U.S. Cl.
CPC ........ *A61B 5/02156* (2013.01); *A61B 5/0215* (2013.01); *A61B 5/7282* (2013.01);
(Continued)

(58) Field of Classification Search
CPC ..... A61B 5/02156; A61B 5/742; A61B 5/746; A61B 5/7282; A61B 5/0215; A61B 5/7275

See application file for complete search history.

(56) References Cited

U.S. PATENT DOCUMENTS 5,006,835 A * 4/1991 Griswold ............. A61B 5/0215
340/626
5,343,868 A * 9/1994 Kurscheidt .......... A61B 5/0215
600/485
(Continued)

FOREIGN PATENT DOCUMENTS

JP     H06-7308 A      1/1994
JP     2006-102237 A   4/2006
(Continued)

OTHER PUBLICATIONS

European Search Report for Application No. EP 15 19 2579 dated Mar. 11, 2016.

(Continued)

*Primary Examiner* — Andrey Shostak

(74) *Attorney, Agent, or Firm* — Pearne & Gordon, LLP

(57) ABSTRACT

A measuring device includes a measuring part that performs an invasive blood pressure measurement using a transducer and detects that a blood pressure measured by the invasive blood pressure measurement becomes a predetermined abnormal state during the invasive blood pressure measurement, a detecting part that detects whether or not a zero-point calibration of the transducer is being carried out, and a notification control part that controls whether or not to output an alarm based on a detection state of the detecting part when the blood pressure becomes the predetermined abnormal state.

12 Claims, 5 Drawing Sheets

(52) U.S. Cl.
CPC .............. *A61B 5/742* (2013.01); *A61B 5/746* (2013.01); *A61B 5/7275* (2013.01)

(56) References Cited

U.S. PATENT DOCUMENTS

| | | | |
|---|---|---|---|
| 11,253,160 B2* | 2/2022 | Shinohara | A61B 5/746 |
| 2006/0074369 A1 | 4/2006 | Oishi et al. | |
| 2010/0026510 A1* | 2/2010 | Kiani | A61B 5/1455 |
| | | | 340/691.3 |
| 2011/0224531 A1 | 9/2011 | Steiner et al. | |
| 2011/0270058 A1* | 11/2011 | Price | A61B 5/021 |
| | | | 600/324 |
| 2012/0065482 A1* | 3/2012 | Robinson | A61B 5/150221 |
| | | | 600/309 |
| 2012/0284208 A1* | 11/2012 | Blomqvist | H04M 15/851 |
| | | | 709/224 |
| 2012/0289808 A1 | 11/2012 | Hubinette | |
| 2013/0285812 A1* | 10/2013 | Rantala | A61B 5/0215 |
| | | | 340/573.1 |
| 2014/0024956 A1* | 1/2014 | Purdy | A61B 5/02154 |
| | | | 600/488 |
| 2015/0284276 A1* | 10/2015 | Ongeche | C02F 1/4602 |
| | | | 210/663 |

FOREIGN PATENT DOCUMENTS

| | | |
|---|---|---|
| JP | 2011-183156 A | 9/2011 |
| JP | 2013-517863 A | 5/2013 |

OTHER PUBLICATIONS

Japanese Office Action issued in Patent Application No. JP-2014-227656 dated Dec. 25, 2017.
Japanese Office Action issued in Patent Application No. JP-2014-227656 dated May 7, 2018.
European Office Action issued in Patent Application No. EP-15 192 579.9 dated Jan. 23, 2018.
Japanese Office Action issued in Patent Application No. JP-2014-227656 dated Sep. 10, 2018.
Chinese Office action issued in Patent Application No. 201510732276.3 dated Jun. 25, 2019.

\* cited by examiner

MEASURING DEVICE, METHOD OF MEASURING BLOOD PRESSURE, AND PROGRAM

CROSS REFERENCE TO RELATED APPLICATION

This application is based on Japanese Patent Applications No. 2014-227656 filed on Nov. 10, 2014, the contents of which are incorporated herein by reference.

BACKGROUND

The present invention relates to a measuring device, a method of measuring a blood pressure and a program.

An invasive blood pressure measuring method is known in which a catheter or the like is inserted in a blood vessel of a subject so that a blood vessel varied from moment to moment is continuously measured (e.g., see JP-A-2013-517863). A pressure generated inside the blood vessel is converted to an electrical signal by a transducer connected to the catheter. Such a blood pressure manometer displays a blood pressure value or blood pressure waveform, which corresponds to an electrical signal converted by the transducer, to medical personnel or the like.

In the invasive blood pressure measurement, a processing referred to as a zero-point calibration for defining a measurement reference value is necessary. The zero-point calibration is carried out by arranging the transducer at a reference point and then defining, as the measurement reference value (e.g., 0 mmHg), an electrical signal corresponding to a blood pressure value when a pressure applied on the transducer is set to zero (the catheter is exposed to the atmosphere).

And now, when the invasive blood pressure measurement is performed, outputting of an alarm for notifying separation of the catheter attached to a patient is recommended. Medical personnel can instantly recognize separation of the catheter by referring to the alarm.

As described above, in such a blood pressure measuring system, a function of detecting separation of the catheter and then outputting an alarm are required.

This function is configured so that the alarm is outputted after a predetermined period of time (e.g., about 10 seconds) passes since a predetermined abnormal state (for example, a state where there is no detected pulse and an average blood pressure is 10 mmHg or less) has been caused.

However, when medical personnel carry out the zero-point calibration, this situation is likely to be decided as the abnormal state as described above. In this case, the alarm is outputted every time the zero-point calibration is carried out. Namely, there is a problem in that useless ringing of alarm is increased.

The problem is illustrated as in FIG. 5. FIG. 5 is a view showing a blood pressure fluctuation and an alarming operation when the zero-point calibration is carried out during a blood pressure measurement. Even while medical personnel carry out the zero-point calibration, an alarm is rung after a blood pressure drop (t31) has been detected (t32). Namely, useless ringing of alarm is occurred.

Accordingly, the present invention has been made keeping in mind the above problems, and a main object thereof is to provide a measuring device, a method of measuring a blood pressure and a program, which can output a proper alarm even if a zero-point calibration is being carried out.

SUMMARY

According to an aspect of the present invention, a measuring device includes a measuring part that performs an invasive blood pressure measurement and detects that a blood pressure measured by the invasive blood pressure measurement becomes a predetermined abnormal state during the invasive blood pressure measurement, a detecting part that detects whether or not a zero-point calibration of the transducer used is being carried out, and a notification control part that controls whether or not to output an alarm based on a detection state of the detecting part when the blood pressure becomes the predetermined abnormal state.

The detecting part detects whether or not the zero-point calibration is being carried out. Also, the measuring part measures a blood pressure value and detects a predetermined abnormal state of the blood pressure. The notification control part controls ringing of alarm based on both of a carrying-out situation of the zero-point calibration and a state of the blood pressure. Thus, it is possible to avoid a situation where an alarm is rung during the zero-point calibration (in other words, useless ringing of alarm is occurred).

The present invention can provide a measuring device, a method of measuring a blood pressure and a program, which can output a proper alarm even if a zero-point calibration is being carried out.

DETAILED DESCRIPTION OF EMBODIMENTS

Embodiment 1

Figure 1:
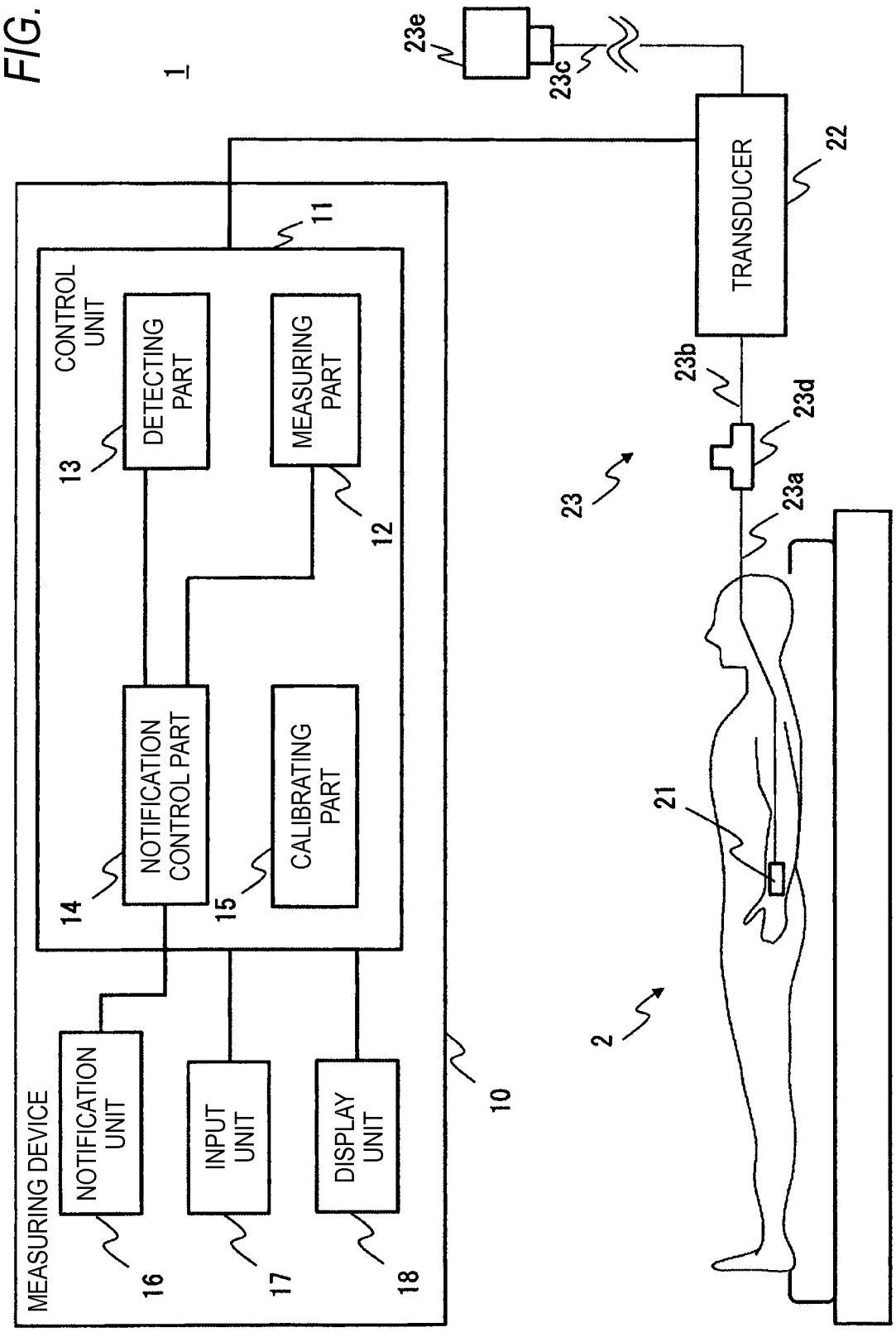
FIG. 1 is a block diagram showings configurations of a blood pressure measuring system 1 according to an embodiment 1.

Embodiments of the present invention will be now described with reference to the accompanying drawings. FIG. 1 is a block diagram showing configurations of a blood pressure measuring system 1 according to the present embodiment. The blood pressure measuring system 1 is configured to invasively measure a blood pressure value of a subject 2. The blood pressure measuring system 1 has a measuring device 10. The measuring device 10 is preferable if the device can invasively measure a blood pressure, and for example, corresponds to a patient monitor, defibrillator or the like. It will be apparent that the measuring device 10 may have configurations capable of performing various measurements (such as body temperature measurement, SpO2, electrocardiogram, and breath curve), in addition to the invasive blood pressure measurement.

A shown example is a case of measuring an artery pressure, in which a catheter (artery needle) 21 is inserted in a radial artery of the subject 2. A transducer 22 is fixed at a height of a heart of the subject 2 (i.e., a height of a location corresponding to a half of a chest thickness). The catheter 21 and the transducer 22 are connected to a monitoring line 23.

The monitoring line 23 includes a first tube 23a, a second tube 23b, a third tube 23c, a three-way stopcock 23d and a fluid bottle 23e. The first tube 23a connects the catheter 21 with the three-way stopcock 23d. The second tube 23b connects the transducer 22 with the three-way stopcock 23d. The three-way stopcock 23d connects the first tube 23a with the second tube 23b to block out the atmosphere during measuring of a blood pressure. Also, the three-way stopcock 23d is plugged to expose the transducer 22 to the atmosphere during being carried out of a zero-point calibration. The third tube 23c connects the fluid bottle 23e with the transducer 22. The fluid bottle 23e contains a heparin-containing saline solution.

The transducer 22 is a transducer used to invasively measure a blood pressure. The transducer 22 outputs an electrical signal corresponding to a pressure in a blood vessel of the subject 2 transmitted thereto through the heparin-containing saline solution. The measuring device 10 displays a blood pressure value or blood pressure waveform, which corresponds to the electrical signal, to a user such as medical personnel.

The measuring device 10 has a control unit 11, a notification unit 16, an input unit 17 and a display unit 18. The control unit 11 includes a measuring part 12, a detecting part 13, a notification control part 14 and a calibrating part 15. Also, the measuring device 10 appropriately has a secondary memory device and the like, not shown.

The notification unit 16 is intended to output a voice guidance or alarm and for example is constituted of a speaker, a speaker-peripheral circuit and the like. Alternatively, the notification unit 16 is not limited to outputting a sound, but may be configured to visually notify a warning, for example, as in an indicator. The output processing of the notification unit 16 is controlled by the notification control part 14, as described below. The input unit 17 is an interface for receiving a data input from medical personnel.

For example, the input unit 17 is buttons, knobs, switches and the like provided on a housing of the measuring device 10. Also, the input unit 17 may be configured to be integrated with a display device (liquid crystal display) as in a touch panel. The input unit 17 includes button for a zero-point calibration and buttons for an all-zero processing as described below.

The display unit 18 includes a display device and a peripheral circuit (or software) for displaying various measurement values or display messages of the measuring device 10. The display unit 18 may be a liquid crystal display or an indicator provided on the housing of the measuring device 10 and also may be a display device removably provided on the measuring device 10.

Next, operations of each of processing parts in the control unit 11 will be described. The control unit 11 is intended to control the measuring device 10 and is configured to appropriately read out and execute a program from a memory unit (secondary memory device) not shown. For example, the control unit 11 performs a displaying control during being carried out of a zero-point calibration.

The calibrating part 15 corrects a measurement reference value for a blood pressure value to be measured by the measuring device 10. At a point of time, such as starting of a blood pressure measurement, a zero-point calibration of the measuring device 10 is performed. Specifically, the three-way stopcock 23d is switched to an exposed state to the atmosphere, so that a pressure applied on the transducer 22 becomes zero. The calibrating part 15 performs an internal calibration so that an electrical signal inputted to the measuring device 10 in such a state is set to as a reference value (e.g., 0 mmHg).

The measuring part 12 performs an invasive blood pressure measurement. Namely, the measuring part 12 calculates a blood pressure value or blood pressure waveform of the subject 2 on the basis of data obtained by digitally converting the electrical signal outputted from the transducer 22. A method for calculating the blood pressure value or blood pressure waveform is preferably identical to a technique in a typical invasive blood pressure measurement. The calculated blood pressure value or blood pressure waveform is displayed on the display unit 18.

Also, the measuring part 12 detects that the subject 2 is in a predetermined abnormal state on the basis of the calculated blood pressure value or blood pressure waveform. Herein, the predetermined abnormal state is a state where separation of the catheter 21 from the patient is occurred or the like. For example, the predetermined abnormal state is a case where a state in which there is no pulse and an average blood pressure value is 10 mmHg or less is continued during a predetermined period of time or more (e.g., about 10 seconds).

The detecting part 13 detects whether or not the zero-point calibration is being carried out. For example, the detecting part 13 decides whether or not the zero-point calibration is being carried out in accordance with the following technique.

(1) Pushing of a "Zero-Point Calibration/All-Zero" Button

The detecting part 13 monitors an input interface (button, knob, or switch) associated with the zero-point calibration, thereby deciding that the zero-point calibration is being carried out when an operation thereof indicating that the zero-point calibration is carried out is performed.

(2) Executing of a Zero-Point Calibration Processing

The detecting part 13 monitors operation of the calibrating part 15, thereby detecting that the zero-point calibration is being carried out (e.g., a software for the zero-point calibration is being executed).

(3) Displaying of a Message Related to the Zero-Point Calibration

The detecting part 13 monitors a displaying instruction, which is sent from the calibrating part 15 to the display unit 18 and is related to that the zero-point calibration is being carried out, or a message displaying processing in the display unit 18 related to that the zero-point calibration is being carried out. Further, the detecting part 13 decides that the zero-point calibration is being carried out when a massage indicating that the zero-point calibration is being carried out is displayed. Also, the detecting part 13 decides that the zero-point calibration is being carried out when a dedicated screen for the zero-point calibration is displayed on the display unit 18. In addition, the detecting part 13 decides that the zero-point calibration has been ended when an ending massage of the zero-point calibration is displayed.

(4) Detection of an All-Zero Operation

A detecting method related to the all-zero is used in a case where a plurality of catheters 21 are used to perform an invasive blood pressure measurement at a plurality of locations. The detecting part 13 decides that the zero-point calibration is being carried out when the all-zero operation (operation of being carried out the zero-point calibration at the plurality of locations) by a software is detected.

Figure 2:
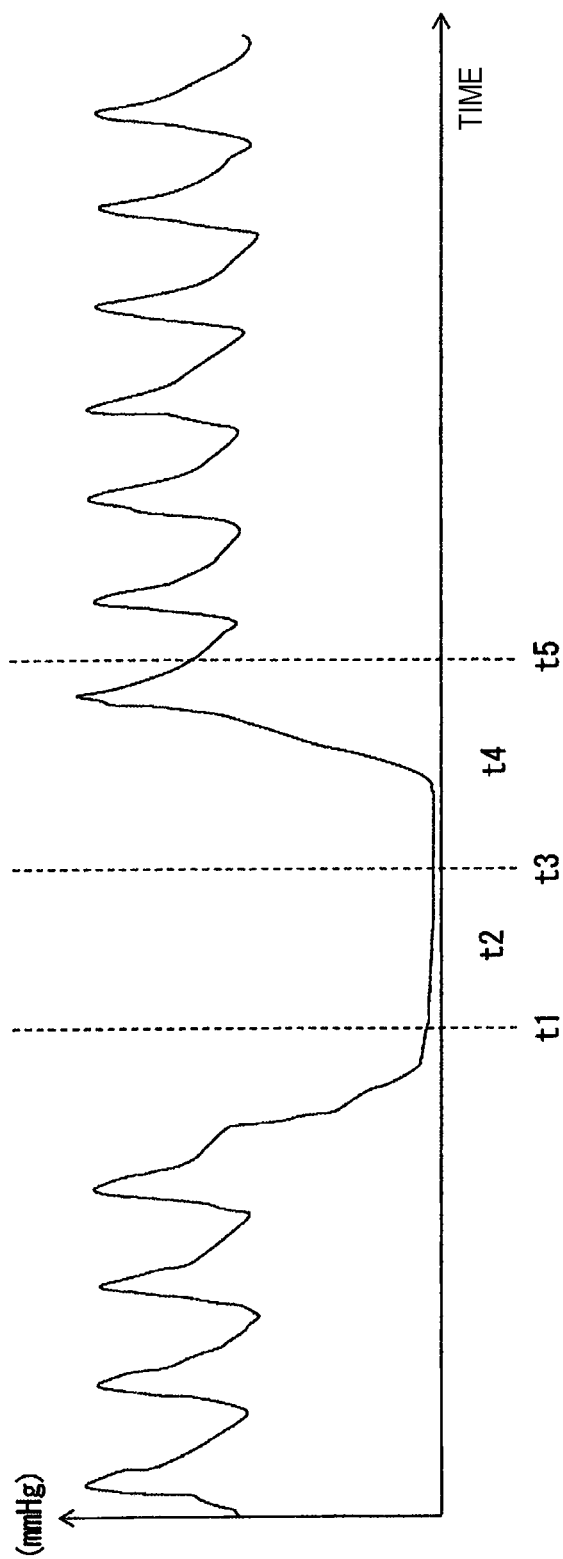
FIG. 2 is a conceptual view showing a method of detecting a zero-point calibration by a detecting part 13 according to the embodiment 1.

An operation image of the detecting part 13 is newly described with reference to FIG. 2. FIG. 2 is an example of a blood pressure waveform representing fluctuation of blood pressure values measured by the invasive blood pressure measurement. At time t1, the detecting part 13 detects that the zero-point calibration is being carried out when a button for the "zero-point calibration" or an interface for the "all-zero operation" is operated. Also, at a time t2, the detecting part 13 detects that the zero-point calibration is being carried out when a message related to that the zero-point calibration is being carried out is displayed from the display unit 18.

It is assumed that the zero-point calibration is ended at a time t3. At a time t4, the detecting part 13 decides that the zero-point calibration has been ended when a message ("zero-point calibration completion", "change in zero value", "outside of zero value range" or the like) related to ending of the zero-point calibration is displayed. Also, at a time t5, the detecting part 13 decides that the device has returned to a normal measurement when displaying the massage related to ending of the zero-point calibration is ended.

The foregoing is the method of detecting that the zero-point calibration is being carried out by the detecting part 13. Alternatively, the detecting part 13 may employ any other detecting techniques so long as it is possible to detect that the zero-point calibration is being carried out. The detecting part 13 notifies whether or not the zero-point calibration is being carried out to the notification control part 14 in real time.

Again referring to FIG. 1, the notification control part 14 controls outputting of alarm by the notification unit 16 on the basis of a detection state of the zero-point calibration by the detecting part 13 and a detection state of the predetermined abnormal state by the measuring part 12. Next, a control image will be described with reference to FIGS. 3 and 4.

Figure 3:
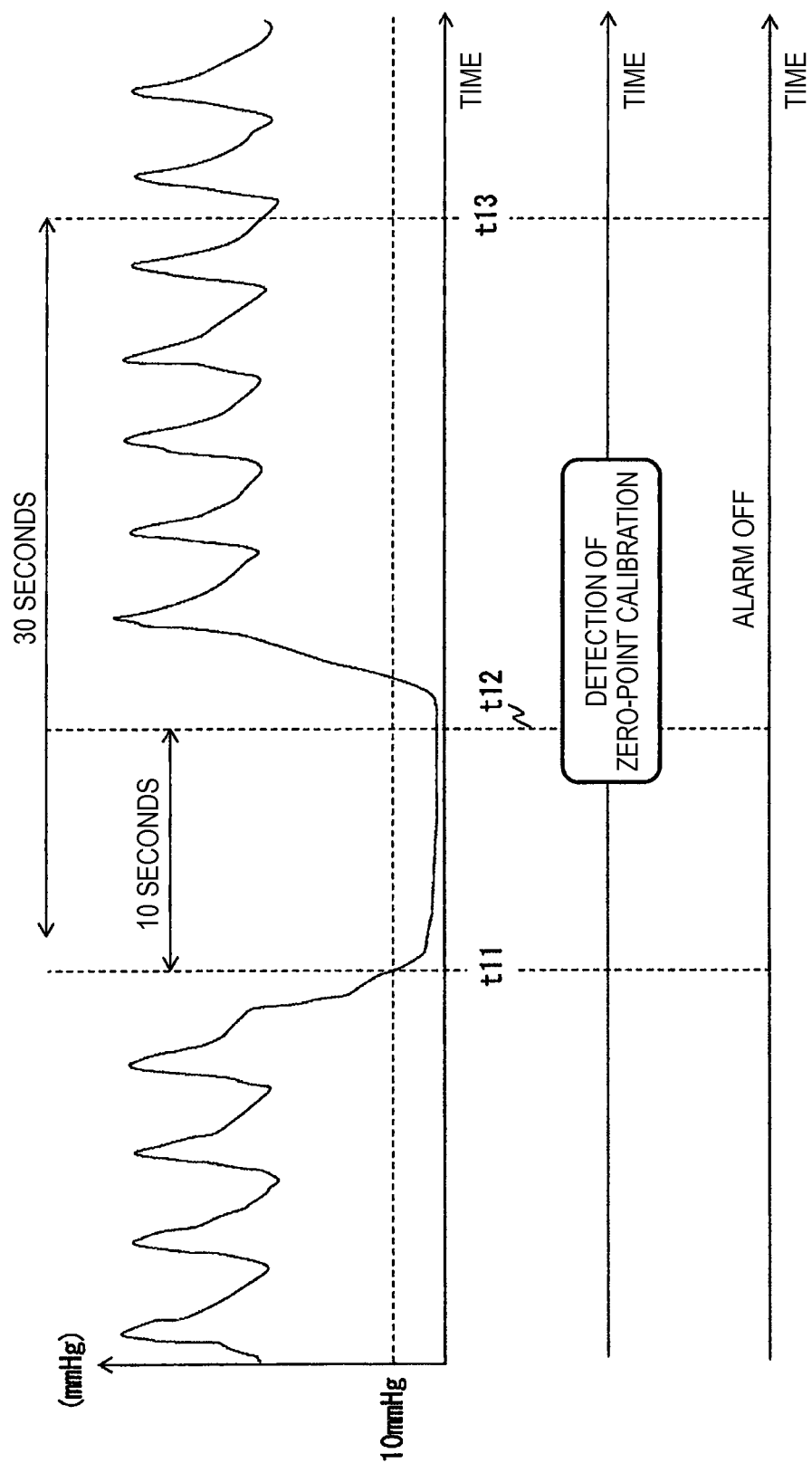
FIG. 3 is a conceptual view showing a ringing control of alarm by a notification control part 14 according to the embodiment 1.

FIG. 3 is a conceptual view showing a first operation example of the notification control part 14. The measuring part 12 continuously measures a blood pressure value or blood pressure waveform. The measuring part 12 detects that an average blood pressure value becomes 10 mmHg or less and there is no detected pulse (t11). Also, the measuring part 12 detects that a predetermined period of time (e.g., 10 seconds) passes since there has been no longer a pulse and the average blood pressure value has become 10 mmHg or less (a predetermined value or less). At the approximately same time, the detecting part 12 detects that the zero-point calibration is being carried out in accordance with the foregoing technique.

At a time t12, the notification control part 14 decides that the zero-point calibration is being carried out, although the state where there is no pulse and the average blood pressure value is 10 mmHg or less is continued during a predetermined period of time or more. Because the zero-point calibration is being carried out, the notification control part 14 controls alarm related to separation of the catheter not to be rung at the time t12 (alarm OFF).

Alternatively, the notification control part 14 may control the alarm in consideration of the zero-point calibration at the timing (t11) at which there is no longer a pulse and the average blood pressure value becomes 10 mmHg or less. However, a case where a blood pressure value is temporarily dropped but the blood pressure waveform is raised due to operation of the circulator of the subject 2 has to be considered. Thus, outputting of the alarm is preferably controlled after a predetermined period of time passes since the average blood pressure value has become the predetermined value or less as shown in FIG. 3 (t12).

The notification control part 14 again controls the alarm at a timing (t13) after a predetermined period of time (after 30 seconds in the present example) from a predetermined timing. At the time t13, the measuring part 12 detects that the average blood pressure value is 10 mmHg or more or there is a pulse. Namely, the measuring part 12 detects that the blood pressure returns to a typical blood pressure state. Accordingly, at the time t13, the notification control part 14 decides that the current state is a normal state and thus controls the alarm not to be rung (alarm OFF).

Meanwhile, the predetermined timing (timing at which the 30-second counting is started) may be a timing of t1 to t5 in FIG. 2 as described above, t11 in FIG. 3 or the like. Namely, the predetermined timing corresponds for example to the followings.

(A) An operating timing of interfaces for the "zero-point calibration" or the "all-zero".
(B) Starting displaying a message related to that the zero-point calibration is being carried out.
(C) Ending of the zero-point calibration,
(D) Starting displaying a message related to ending of the zero-point calibration.
(E) Ending displaying the message related to ending of the zero-point calibration.
(F) Initiating of the predetermined abnormal state (t11 in FIG. 3).

The 30 seconds means a period of time sufficient to end the zero-point calibration, and thus 25 seconds or the like may be employed. In other words, the operations as described above are as follows. The measuring part 12 decides whether or not the average blood pressure value becomes again the predetermined abnormal state after suppressing the alarm by the zero-point calibration (t13 in FIGS. 3 and t2 in FIG. 4 as described below). The notification control part 14 controls an alarm not to be rung when the average blood pressure value is decided as being in a normal state. Alternatively, the notification control part 14 may control the alarm to be rung if the average blood pressure value is decided as becoming again the predetermined abnormal state.

Figure 4:
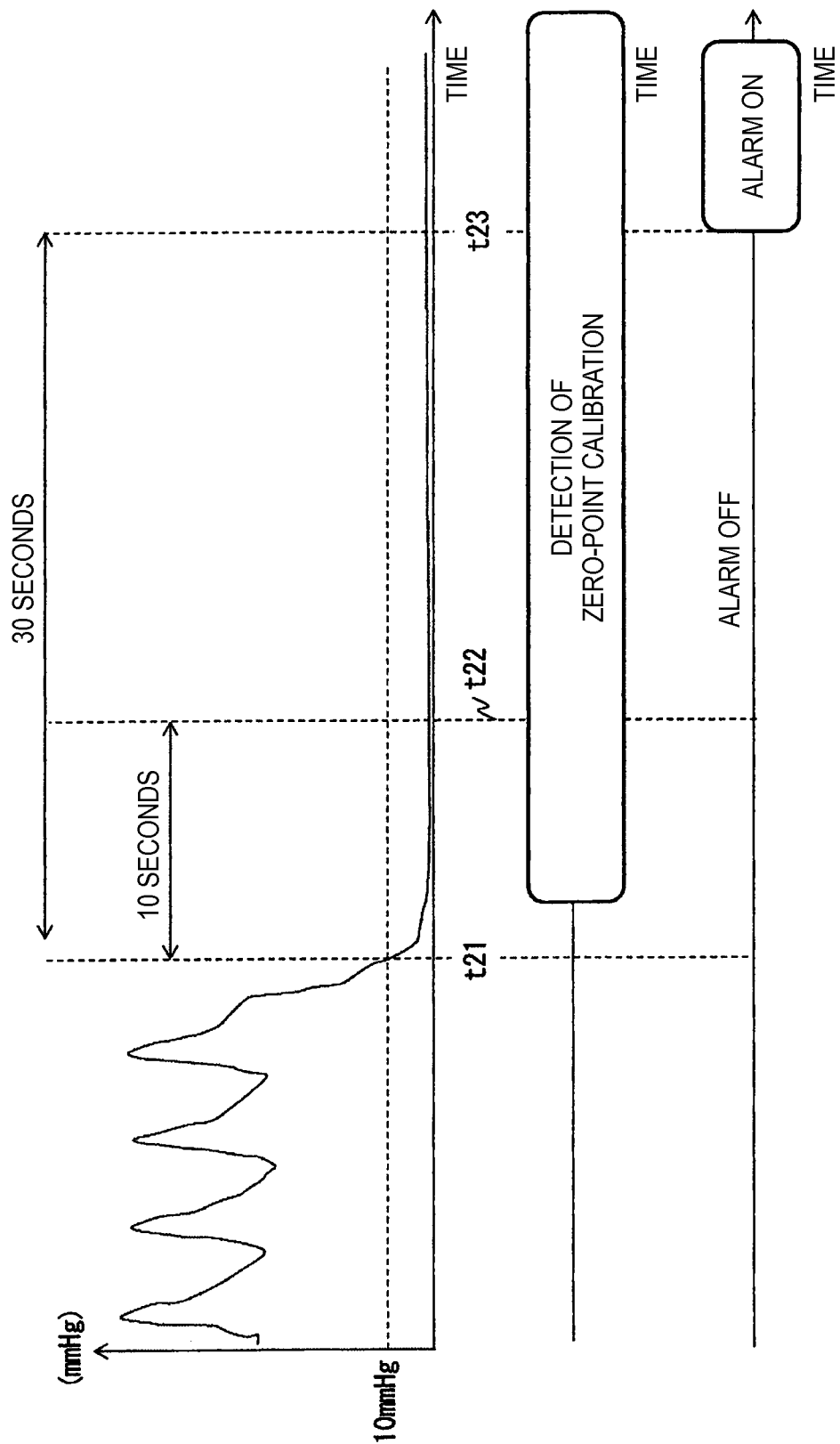
FIG. 4 is a conceptual view showing a sounding control of alarm by the notification control part 14 according to the embodiment 1.
Figure 5:
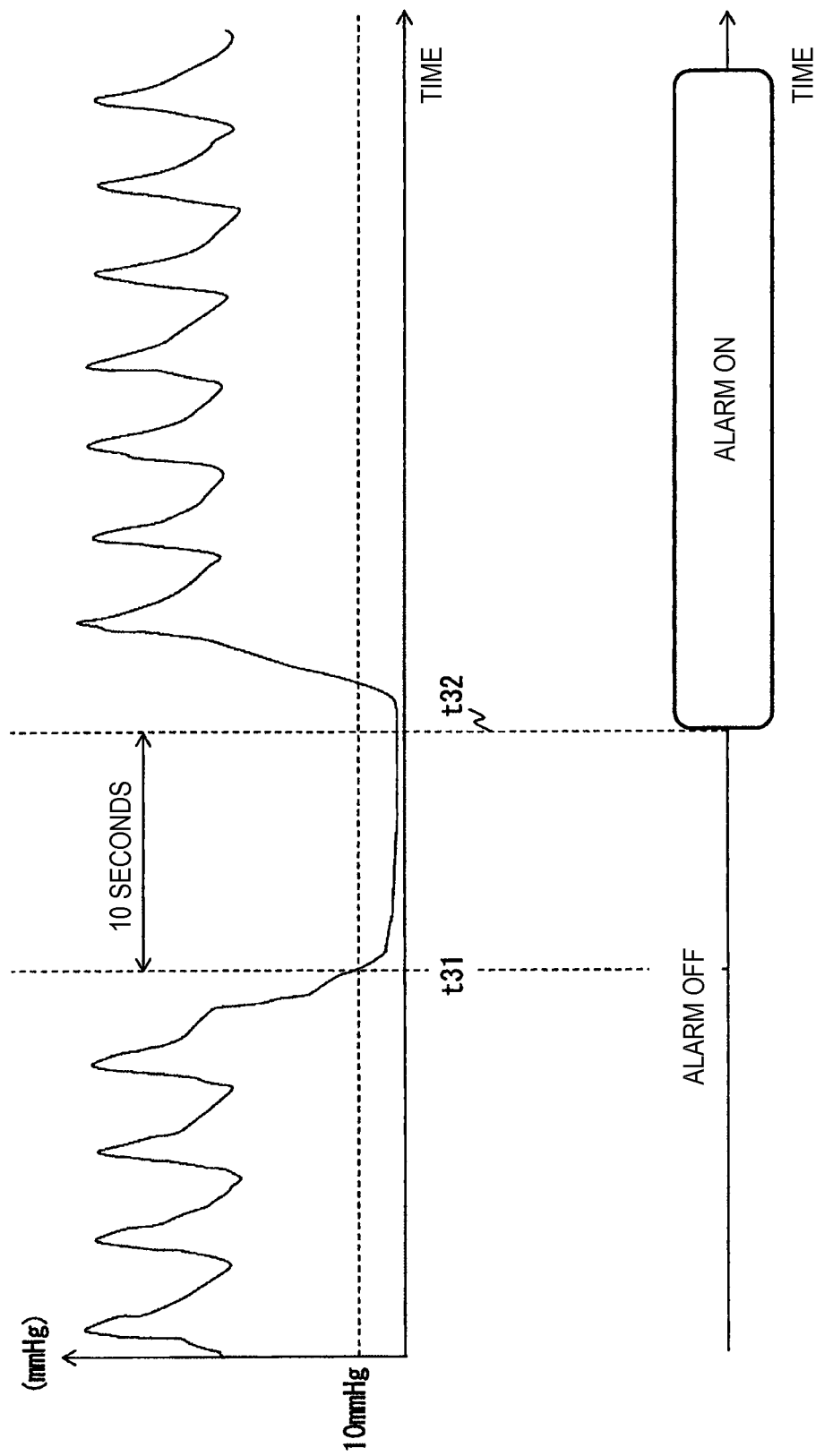
FIG. 5 is a conceptual view showing an aspect of alarm rung in a typical measuring device.

FIG. 4 is a conceptual view showing a second operation example of the notification control part 14. The measuring part 12 detects that an average blood pressure value becomes 10 mmHg or less and there is no detected pulse (t21). Also, the measuring part 12 detects that a state where there is no pulse and the average blood pressure value is 10 mmHg or less is continued during a predetermined period of time (e.g., 10 seconds) (t22). However, at the time t22, the notification control part 14 controls an alarm related to separation of the catheter not to be rung, because the zero-point calibration is being carried out (alarm OFF).

The notification control part 14 also controls the alarm at a timing (t23) after 30 seconds from the predetermined timing. The detecting part 13 notifies to the notification control part 14 that the zero-point calibration is still being carried out. Also, the measuring part 12 notifies to the notification control part 14 that the average blood pressure value is still 10 mmHg or less. Because the average blood pressure value is still lower, the notification control part 14 controls the alarm to be rung even if it is decided that the zero-point calibration is being carried out (t23, alarm ON). In this way, the notification control part 14 controls the alarm to be outputted when the average blood pressure value is still lower even if some time passes after suppressing the alarm.

The foregoing is the detailed operation of the notification control part 14. In this way, the notification control part 14 controls ringing of alarm depending on whether or not the zero-point calibration is being carried out. Meanwhile, if not shown, the notification control part 14 rings an alarm about a typical separation of the catheter if the average blood pressure value becomes 10 mmHg or less while detection of the zero-point calibration is not carried out. Also, although a threshold value of the average blood pressure value is described as 10 mmHg in the foregoing description, the present invention may employ any other values if the values have a gap from average blood pressure values of healthy people.

Next, the effects of the measuring device 10 according to the present embodiment will be described. As described above, the detecting part 13 detects whether or not the zero-point calibration is being carried out. Also, the measuring part 12 measures a blood pressure value and detects the predetermined abnormal state. The notification control part 14 controls ringing of alarm based on both of a carrying-out situation of the zero-point calibration and a state of the blood pressure. Thus, it is possible to avoid a situation where an alarm is rung during the zero-point calibration (in other words, useless ringing of alarm is occurred).

Also, the notification control part 14 rings alarm if a state where the zero-point calibration is being carried out is continued during a predetermined period of time (i.e., t23 in FIG. 4) (alarm ON). Thus, medical personnel can recognize separation of the catheter 21 during carrying out of the zero-point calibration or forgetting returning the three-way stopcock 23.

In the foregoing, the invention achieved by the present inventors has been described in detail based on the embodiments, but it will be apparent that the present invention is not limited to the embodiments described above and various modifications thereof can be made without departing from the spirit thereof.

Meanwhile, some or all of the processing of the control unit 11 in the measuring device 10 may be embodied as computer programs which are operated in the measuring device 10. For example, the measuring part 12 calculates a blood pressure value or blood pressure waveform using data digitalized by A/D-converting a blood pressure signal outputted from the transducer 22.

Herein, the program can be stored using various types of non-transitory computer readable media and be supplied to a computer. The non-transitory computer readable media include various types of tangible storage media. Examples of non-transitory computer readable media include magnetic recording media (e.g., a flexible disk, a magnetic tape, a hard disk drive), magneto-optical recording media (e.g., a magneto-optical disk), CD-ROM (Read Only Memory), CD-R, CD-R/W, semiconductor memories (e.g., mask ROM, PROM(Programmable ROM), EPROM(Erasable PROM), flash ROM, RAM(random access memory)). Also, the program may be supplied to the computer by various types of transitory computer readable media. Examples of transitory computer readable media include electrical signals, optical signals and electromagnetic waves. The transitory computer readable media can supply the program to the computer through a wire communication path, such as electric wires or optic fibers, or a wireless communication path.

What is claimed is:

1. A measuring device, comprising:
an input device configured to receive a user input to perform a zero-point calibration of a transducer;
a display;
an alarm configured to be output during an abnormal invasive blood pressure measurement; and
a controller configured to:
perform the zero-point calibration of the transducer upon receiving the user input;
control the invasive blood pressure measurement using the transducer;
detect that the invasive blood pressure measurement is abnormal and that the zero-point calibration of the transducer is being carried out, the invasive blood pressure measurement being abnormal during the zero-point calibration;
display a message indicating a change in a zero value or a value outside of a zero value range on the display; and
suppress the alarm based on the message on the display.

2. The measuring device according to claim 1, wherein the controller is configured to detect that the invasive blood pressure measurement is abnormal when, during the invasive blood pressure measurement, there is no detected pulse and an averaged blood pressure measurement value is a predetermined value or less.

3. The measuring device according to claim 2, wherein the predetermined value is 10 mmHg.

4. The measuring device according to claim 1, wherein the controller is configured to detect that the invasive blood pressure is abnormal when, during the invasive blood pressure measurement, there is no detected pulse and an averaged blood pressure measurement value is a predetermined value or less for at least a predetermined period of time.

5. The measuring device according to claim 1, wherein the controller is further configured to output the alarm when the blood pressure measurement is abnormal while the zero-point calibration is not detected.

6. The measuring device according to claim 1, wherein the controller is further configured to perform the zero-point calibration by correcting a measurement reference value for the blood pressure.

7. The measuring device according to claim 1, wherein the controller is configured to determine, in real time, that the zero-point calibration is being performed.

8. The measuring device according to claim 1, wherein the input device is a user interface.

9. The measuring device according to claim 1, wherein the controller is configured to detect that the zero-point calibration is being performed when the message is displayed on the display.

10. The measuring device according to claim 1, wherein the message indicates an ending of the zero-point calibration being performed.

11. A method of measuring a blood pressure, comprising:
performing a zero-point calibration of a transducer upon receiving a user input;
performing an invasive blood pressure measurement using the transducer;
detecting that the invasive blood pressure measurement is abnormal and that the zero-point calibration of the transducer is being carried out, the invasive blood pressure measurement being abnormal during the zero-point calibration;
displaying a message indicating a change in a zero value or a value outside of a zero value range on a display; and
suppressing an alarm based on the message on the display, the alarm being configured to be output during the abnormal invasive blood pressure measurement.

12. A non-transitory computer readable medium storing a program causing a computer to execute a process comprising:
- performing a zero-point calibration of a transducer upon receiving a user input;
- performing an invasive blood pressure measurement using the transducer;
- detecting that the invasive blood pressure is abnormal and that the zero-point calibration of the transducer is being carried out, the invasive blood pressure measurement being abnormal during the zero-point calibration;
- displaying a message indicating a change in a zero value or a value outside of a zero value range on a display; and
- suppressing an alarm based on the message on the display, the alarm being configured to be output during the abnormal invasive blood pressure measurement.

* * * * *